(12) United States Patent
Jones et al.

(10) Patent No.: US 10,231,457 B2
(45) Date of Patent: Mar. 19, 2019

(54) CALCIUM HYPOCHLORITE COMPOSITIONS WITH TRANSIENT COLOR INDICATORS AND METHOD OF USING THE SAME

(71) Applicant: Arch Chemicals, Inc., Allendale, NJ (US)

(72) Inventors: Janet Jones, Columbia, MO (US); Amber Khanzada, Alpharetta, GA (US); Janet Akande, Fayetteville, GA (US); Michael J. Unhoch, Tyrone, GA (US)

(73) Assignee: ARCH CHEMICALS, INC., Allendale, NJ (US)

( * ) Notice: Subject to any disclaimer, the term of this patent is extended or adjusted under 35 U.S.C. 154(b) by 522 days.

(21) Appl. No.: 15/003,248

(22) Filed: Jan. 21, 2016

(65) Prior Publication Data
US 2016/0205938 A1 Jul. 21, 2016

Related U.S. Application Data

(60) Provisional application No. 62/106,010, filed on Jan. 21, 2015.

(51) Int. Cl.
*A01N 59/06* (2006.01)
*C02F 1/68* (2006.01)
*C02F 1/76* (2006.01)
*C02F 103/42* (2006.01)

(52) U.S. Cl.
CPC .............. *A01N 59/06* (2013.01); *C02F 1/688* (2013.01); *C02F 1/76* (2013.01); *C02F 2103/42* (2013.01); *C02F 2303/04* (2013.01)

(58) Field of Classification Search
CPC ..... A01N 59/06; C01B 11/064; C01B 11/068; C02F 1/68; C02F 1/687; C02F 1/688; C02F 1/50; C02F 1/76; C02F 2209/00; C02F 2209/04; C02F 2209/29
See application file for complete search history.

(56) References Cited

U.S. PATENT DOCUMENTS

| | | | |
|---|---|---|---|
| 3,741,805 A | 6/1973 | Crotty et al. | |
| 3,793,216 A | 2/1974 | Dychdala et al. | |
| 4,145,306 A | 3/1979 | Tatara et al. | |
| 4,192,763 A | 3/1980 | Buchan | |
| 4,201,756 A | 5/1980 | Saeman et al. | |
| 4,248,827 A | 2/1981 | Kitko | |
| 4,587,069 A | 5/1986 | Meloy | |
| 4,683,072 A | 7/1987 | Holdt et al. | |
| 4,692,335 A | 9/1987 | Iwanski | |
| 4,865,760 A | 9/1989 | Johnson et al. | |
| 4,876,003 A | 10/1989 | Casberg | |
| 4,928,813 A | 5/1990 | Casberg | |
| 4,961,872 A | 10/1990 | Sinclair | |
| 5,009,806 A | 4/1991 | Johnson et al. | |
| 5,049,385 A | 9/1991 | Wiedrich et al. | |
| 5,106,559 A | 4/1992 | Wiedrich et al. | |
| 5,164,109 A | 11/1992 | Wojtowicz | |
| 5,338,461 A * | 8/1994 | Jones ...................... | C02F 1/76 210/755 |
| 5,685,262 A | 11/1997 | Stevenson | |
| 5,753,602 A | 5/1998 | Hung et al. | |
| 5,756,440 A | 5/1998 | Watanabe et al. | |
| 6,528,466 B1 | 3/2003 | Lan et al. | |
| 7,820,198 B2 | 10/2010 | Blanchette et al. | |
| 2003/0059483 A1 | 3/2003 | Sowle et al. | |
| 2004/0163608 A1 | 8/2004 | Freedman et al. | |
| 2007/0125979 A1* | 6/2007 | Lei .......................... | C02F 1/76 252/176 |
| 2008/0258104 A1 | 10/2008 | Mullins et al. | |
| 2009/0196939 A1 | 8/2009 | Hei et al. | |
| 2012/0301555 A1 | 11/2012 | Walls | |
| 2013/0178474 A1 | 7/2013 | Unhoch et al. | |

FOREIGN PATENT DOCUMENTS

| | | |
|---|---|---|
| GB | 1041593 A | 9/1966 |
| GB | 1049051 A | 11/1966 |
| JP | H05140590 A | 6/1993 |
| WO | 8905093 A1 | 6/1989 |
| WO | 90/00006 A1 | 1/1990 |
| WO | 9907817 A1 | 2/1999 |

OTHER PUBLICATIONS

International Search Report and Written Opinion for International Application No. PCT/US2016/014284 (dated Apr. 7, 2016) (10 Pages).
The Extended European Search Report from European Patent Office issued in connection with EP Application No. 16740744.4, dated May 23, 2018 (7 pages).

* cited by examiner

*Primary Examiner* — Lucas A Stelling
(74) *Attorney, Agent, or Firm* — Lucas & Mercanti, LLP

(57) ABSTRACT

A water treatment composition for treating a body of water is provided that provides visual feedback to the end-user of the effectiveness of the composition. The composition contains a majority of calcium hypochlorite particles; and an effective amount of colored particles containing an oxidizable pigment oxidizable dye and a water soluble material. The colored particles release the oxidizable dye to the body of the water to provide a transient color to the recreational water during dissolution of the composition in the body of water, the transient color providing a visual cue to the end-user signaling of the biocidal activity of the composition. Also provided is a method of applying the water treatment composition to recreational water.

21 Claims, No Drawings

CALCIUM HYPOCHLORITE COMPOSITIONS WITH TRANSIENT COLOR INDICATORS AND METHOD OF USING THE SAME

CROSS-REFERENCE TO RELATED APPLICATION

This application claims priority under 35 U.S.C. § 119(e) from Provisional Application No. 62/106,010 filed Jan. 21, 2015, which is herein incorporated by reference.

FIELD OF THE INVENTION

The present invention relates to calcium hypochlorite compositions useful for treating recreational water systems and, more particularly, to calcium hypochlorite compositions that exhibit a transient color indicator (i.e., a flash of color) in recreational water systems.

BACKGROUD OF THE INVENTION

Calcium hypochlorite is known for use as a treatment for recreational water systems, such as pools, spas, hot tubs, and the like and other similar water systems. Calcium hypochlorite serves as a source of available chlorine in the form of an pH dependent equilibrium of hypochlorous acid (HOCl) and hypochlorite anions (ClO$^-$), which acts as a biocide to keep the water systems free of water-borne pathogens and other organisms such as algae. The water-borne pathogens and other organisms, if not controlled, can result in unwanted film formation, unwanted clouding of the water and/or can make the water system unusable for its intended purpose. Examples of calcium hypochlorite compositions are shown in various patents such as U.S. Pat. Nos. 3,793,216; 4,201,756; 4,876,003; 4,928,813; 4,145,306; 4,192,763; 4,692,335; 4,865,760; 4,961,872; 5,009,806; 5,164,109; and 5,753,602.

Calcium hypochlorite is available in various forms, including solid granules and solid tablets. Each of these forms has their advantages and disadvantages. Granular forms offer lower shipping weight, less storage space, minimal spill hazards and safer handling. Granular calcium hypochlorite is particularly convenient for shock treatment since the granules can be broadcast over the surface of the water, added to the pool skimmer with the circulation system running, or pre-diluted in water and added to the pool. Calcium hypochlorite in tablet form offers all the advantages of the granular form but is capable of more effectively delivering a continuous level of chlorination.

However, calcium hypochlorite is colorless when dissolved in water. As a result, the end-user is not provided with any type of visual feedback confirming the delivery of the calcium hypochlorite to the water.

While transient color indicators have not been used with recreational water systems, transient color indicators have been used with bleach formulations for cleaning and disinfectant applications. One of the earliest attempts to provide a "flash of color" to cleaning formulations is found in British Publication No. GB 1,049,051. In GB 1,049,051, the applicants incorporated an "indicator dye" into a powder cleaning preparation to provide the end-user with an indicator of the activity of the preparation during use. The cleaning preparation also included chlorine-containing oxidizing agent or a dry oxygen bleaching agent in addition to surfactants. The "indicator dye" is a water-soluble dye that provides an initial color to the water which subsequently disappears after a period of time due to bleaching caused by the bleaching agent. Prior to use, the "indicator dye" is protected from initial bleaching with a water-soluble gum or resin coating. The gum or resin coating may be applied by spray drying the dye particles.

An attempt to provide transient color indicators to disinfectants is found in U.S. Pat. Nos. 4,248,827. 4,248,827 describes a method for sanitizing toilets with a two-part liquid disinfectant system. One chamber of the described dispensing system contains a hypochlorite sanitizing solution. The other chamber contains a dye solution bleachable via oxidation from a colored state to a colorless state. The release of both solutions during the flush cycle is intended to provide transitory visual signal that can last from 5 seconds up to 10 minutes. The liquid formulations can also contain a variety of surfactants, in addition to other agents, to increase sanitizing efficacy.

Another attempt to provide transient color indicators to cleaning formulations is found in International Publication No. WO99/07817. WO99/07817 describes decolorizing compositions as an indicator system for detergent formulations. The decolorizing composition is intended to provide a visual indicator to wash liquor/solvent that decolorizes over a predetermined amount of time. The decolorizing composition is a mixture of dye particles and bleach particles where the bleach particles are provided with at least one binder coating. The binder coating or coatings prevent the dye from being bleached and decolorized thereby controlling the amount of time the visual indicator is presented to the end-user.

In addition, there are halogen-releasing compositions which contain colored salt particles that are added calcium hypochlorite for the purposes of identifying the concentration of the chlorine in the composition. For example, see U.S. Pat. No. 5,049,385. However, the amount of the dye in the salt is such that there is no color change in the water in which the composition is added.

In view of the above, there is a need to provide recreational water systems with a transient color indicator when treated with calcium hypochlorite allowing the end-user to ascertain whether the calcium hypochlorite is dispersed in the recreational water.

SUMMARY OF THE INVENTION

The present invention provides water treatment composition containing calcium hypochlorite that includes a transient color indicator as well as a method of treating a body of water using this water treatment composition. The body of water is a body of water that may need sanitization/disinfecting and includes, for example, recreational bodies of water. In one embodiment, the water treatment composition includes a majority of calcium hypochlorite particles, and an effective amount of particles of an oxidizable pigment, an oxidizable dye or a mixture thereof. The oxidizable pigment and/or oxidizable dye particles provide a transient color to the recreational water during dissolution of the water treatment composition in the water. The transient color provides a visual cue to an end-user of the biocidal activity provided to the body of recreational water by the water treatment composition. The oxidizable pigment and/or oxidizable dye particles may be provided with a water soluble coating or may be adhered or adsorbed onto the surface of a water soluble material. The water-soluble material may serve to inhibit premature bleaching of the oxidizable dye by the calcium hypochlorite particles contained in the water treatment composition prior to administering the water treatment composition to the recreational water. The water treatment composition is also substantially free of surfactants to avoid foaming of the recreational water. In a different embodiment, a body of recreational water is treated by administering to the recreational water a biocidal amount of the water treatment composition described herein.

The water treatment composition may be in the form of granules or in the form of a tablet. As a granular composition, the calcium hypochlorite and colored particles are in a granular form. Alternatively, the granular formula may be tableted as a compacted tablet.

In one embodiment, the water treatment composition contains colored particles which are an oxidizable dye and a water soluble material. The water soluble material may be an inorganic salt, a gum or a resin. In a particular embodiment, the water soluble material is an inorganic salt, in particular sodium chloride.

In another embodiment, the water soluble material may include a first water soluble material and a second water soluble material. The oxidizable pigment and/or oxidizable dye is mixed with the second water soluble material to form a mixture, and the mixture is then coated onto the first water soluble material. The first and second water soluble materials may each be an inorganic salt, in particular sodium chloride.

In a further embodiment, the colored particles make up from about 0.1% by weight to about 10% by weight of the total weight of the water treatment composition. In a particular embodiment, the colored particles make up about 1% to about 6% by weight of the water treatment composition. In these embodiments, the oxidizable dye may be between 0.01 and 2.0% by weight of the composition.

In yet another embodiment, the calcium hypochlorite makes up between about 60% and 99.9% by weight of the total water treatment composition. In a particular embodiment, the calcium hypochlorite makes up between about 75% and 85% by weight of the total weight of the water treatment composition.

In an additional embodiment, the water treatment composition may contain up to 30% by weight, based on the total weight of the composition, of additional active components selected from the group consisting of water clarifiers, scale inhibitors, stabilizers, water softeners, corrosion inhibitors, algaecides, fungicides, binders, or a mixture thereof.

In another embodiment, the present invention provides a method of treating a body of water with a biocidal composition which provides a visual cue to an end-user treating the recreational body of water signifying the effectiveness of the biocidal composition. The method includes administering to the body of water a biocidal amount of the composition of the invention, and allowing the composition to dissolve or disperse in the water to release the pigment or dye into the body of water, providing a transient color to the body of water during dissolution of the composition in the body of water. As previously described, the biocidal composition includes (i) a majority of calcium hypochlorite particles, and (ii) an effective amount of colored particles. The composition is also substantially free of surfactants to avoid foaming of the water. The colored particles may be an oxidizable pigment, an oxidizable dye, a composition of an oxidizable pigment and a water soluble material, a composition of oxidizable dye and a water soluble material, or a mixture thereof. The colored particles release the oxidizable pigment and/or the oxidizable dye to the body of the recreational water to provide a transient color to the recreational water during dissolution of the composition in the body of recreational water. Once again, the transient color provides a visual cue signaling biocidal activity of the composition to the end-user.

The present invention provides several advantages due to the incorporation of the bleachable pigment or dye as a transient color indicator. For example, the end-user will be provided with a visual signal of the biocidal activity provided by the water treatment composition. Depending on the dosage form and method of administration, the length of transient color signal is variable but will last until the water treatment composition is effectively dispersed into the water being treated. These and other advantages will become more apparent from the detailed description discussed below.

DETAILED DESCRIPTION OF THE INVENTION

In accordance with the present invention, a water treatment composition, containing a calcium hypochlorite composition, is provided for treating bodies of water. The body of water may be recreational water such as pools, hot tubs, spas or any other artificial body of water used for recreational purposes. Alternatively, the body of water may be other bodies of water that are non-recreational in nature, but need sanitization, such as ornamental ponds, water fountains and toilet bowls. Generally, the purpose of the composition is for treating recreational bodies of water. The water treatment composition contains a calcium hypochlorite composition that includes a majority of calcium hypochlorite particles, and an effective amount of particles containing an oxidizable pigment, an oxidizable dye or a mixture of the oxidizable pigment and oxidizable dye. The oxidizable pigment and/or oxidizable dye provides a transient color to the recreational water during dissolution of the water treatment composition. The purpose of the transient color is to provide visual feedback or visual cue to the end-user of the biocidal activity the composition delivers to the recreational water and that the composition has been dispersed into the recreational water effectively.

The oxidizable pigment and/or oxidizable dye particles may each include a readily-dissolvable, water-soluble material around the pigment or dye, which may inhibit premature bleaching of the oxidixable pigment and/or oxidizable dye in the composition. The readily-dissolvable, water-soluble material may be a coating on the pigment or dye, or a carrier for the pigment or dye. As a coating, the coating inhibits bleaching of the pigment or dye prior to the composition being administered to the body of recreational water. Alternatively, as a carrier, the pigment or dye is attached to or adsorbed onto a surface of a water-soluble material. In another embodiment, the pigment or dye may be placed on the surface of or absorbed into a readily-dissolvable, water soluble carrier and the carrier with the pigment or dye is then coated with additional readily-dissolvable, water-soluble material, which may be the same or different from the readily-dissolvable, water-soluble material used as the carrier. In addition, the composition is also substantially free of surfactants to avoid possible foaming of the recreational water.

The composition of the invention may contain a majority of calcium hypochlorite particles. A "majority" means at least 50 percent by weight ("wt. %") of the composition is calcium hypochlorite based on the total weight of the composition. The composition may be a granular form or a tablet form. In either form, the calcium hypochlorite can range from 50.0 to 99.9 wt. % based on the total weight of the composition and, more particularly, can range from 60.0% to 99.0% by weight of the composition. Other embodiments, the calcium hypochlorite can be in the range of about 65.0% to about 90% by weight of the composition. In a particular embodiment, the calcium hypochlorite is present in an amount of 75% to 85% by weight of the composition.

The calcium hypochlorite to be used in the composition of the invention can be either anhydrous or hydrated. Anhydrous calcium hypochlorite, which is commercially available, should contain at least about 60% by weight of $Ca(OCl)_2$. Hydrated calcium hypochlorite should contain at least about 50% by weight of $Ca(OCl)_2$ and have a water content ranging from about 4 to about 15 wt. %. Hydrated calcium hypochlorite can be prepared by the methods described, in U.S. Pat. Nos. 3,544,267 and 3,669,984, both of which incorporated by reference in their entireties.

The composition also includes an effective amount of colored particles to provide the body of recreational water with a transient color, signaling to the end-user the biocidal activity that the composition is providing to the water and that the composition has been effectively dispersed into the water being treated. The colored particles may be a pigment or a dye. As used herein, a "pigment" is a water insoluble material, which a "dye" is a water soluble material. If a pigment is used, the pigment may be used alone or with a water soluble material, provided that the pigment is stable in the calcium hypochlorite. Dyes are generally in liquid form, such as an aqueous solution. In the case of dyes, generally the dye needs a water soluble material or a water dispersible material, as a substrate for the dye, which is described in more detail below. In this context, an effective amount refers to an amount of the colored particles that provides a visible but transient color emanating from the composition while the water treatment composition dissolves in the water. The color is transient due to the pigment or dye being bleached as the dye is oxidized by the dissolved calcium hypochlorite. As a result of the transient nature of the color signal is provided but, preferably, does not alter the overall hue or color of the recreational water.

In an embodiment, the colored particles will contain between 6% to 40% by weight of the dye and 60% to 94% by weight of the water soluble material, based on the total weight of the colored particles. In a particular embodiment, the colored particles will contain between 10% to 25% by weight of the dye and 75% to 90% by weight of the water soluble material based on the total weight of the colored particles. In addition, the colored particle will be present in the composition containing the calcium hypochlorite and the colored particles in an amount between 0.1% and 10% by weight, based on the total weight of the composition. In one embodiment, the composition will contain between 1% and 6% by weight of the composition of the colored particles.

In another embodiment, the colored particles containing the oxidizable pigment or oxidizable dye and water soluble material, if present, may also be distinctly visible from the calcium hypochlorite in the composition. In a different embodiment, the coated, colored particles containing the oxidizable dye and water soluble material are not distinctly visible from the calcium hypochlorite in the composition.

The duration of the transient color is variable and is effected by the selection of the oxidizable pigment or oxidizable dye and the size of the pigment or dye particles. The duration of the transient color should be at least one second and can extend up to 2 or 3 minutes or longer. In another embodiment, the duration of the transient color range from 2 seconds to 1 minute. Typically, the color will last between 3 seconds and 30 seconds. In accordance with the invention, any oxidizable pigment may be used, provided that the pigment is stable with the calcium hypochlorite, meaning that the pigment should not react with the calcium hypochlorite during storage. Several are commercially available. A representative pigment which is stable in the calcium hypochlorite is Ultramarine Blue. In the case of oxidizable dyes, the dye is desirably non-reactive with the calcium hypochlorite, or is made to be non-reactive with the calcium hypochlorite with the use of a water soluble or water dispersible material. Representative examples of oxidizable dyes that are commercially available include, but not limited to, Acid Green 5, Acid Green 9, Acid Green 74, Acid Violet 49, Acid Blue 9 and Acid Blue 7. Of these oxidizable dyes, Acid Blue 9 is of particular interest. As will be apparent to one skilled in the art, the average size of the pigment or dye particles will be directly proportional to the duration of the transient color signal. Stated otherwise, an increase in the average size of the pigment or dye particles will increase the duration of the transient color signal provided to the recreational water.

In the present invention, the water soluble material may be an inorganic salt, water soluble resin or gum. Ideally, the water soluble material is readily water soluble, meaning that it will dissolve within 60 seconds of contacting the water. Ideally, the water soluble material should dissolve in less than about 15 seconds, generally within about 1 to about 10 seconds. If a water soluble resin or gum is used, it should be compatible with the calcium hypochlorite, meaning that it should not react with the calcium hypochlorite during storage. Exemplary inorganic salts include sodium chloride, potassium chloride, calcium chloride, and the like. Of these salts, sodium chloride is of particular interest.

In one embodiment, each of the colored dye particles contains an oxidizable dye and with a readily-dissolvable, water-soluble material. The water-soluble material may be a coating place on the dye or are placed on the surface of a water-soluble material. The coating may protect the dye particle from premature bleaching by the calcium hypochlorite prior to the composition being administered to the recreational water. Reference to readily-dissolvable means that the water soluble material, whether a coating or a substrate, dissolves quickly once the particles are exposed to the water. This allows the readily oxidizable dye thereby allowing the transient color (i.e., a flash of color) to emanate from the composition. In one embodiment, the coating should dissolve within a few seconds of the composition contacting the water. In another embodiment, the coating should dissolve within 0-10 seconds of contacting the water in which the composition is placed.

As will be appreciated by those skilled in the art, the actual time frame in which the coatings dissolve is affected by variables such as the coating material and the coating thickness. In one embodiment, the water-soluble coating is a gum or resin, provided that the gum or resin will not adversely react with the calcium hypochlorite.

The water-soluble coatings should have a thickness ranging from about 1 to about 100 microns. Alternatively, the dye may be coated onto the inorganic material, where the inorganic material is in the form of a particle. The coating can be applied by any known method. One suitable method is spray drying the coating onto the dye particles or dye solutions may be spray dried onto inorganic salt particles. Spray drying is known in the art and can be completed by forming a solution of one material, and the solution is sprayed onto the particle.

Generally, the colored particles will have a majority of particles with a particle size which in the range of about 150 microns and 850 microns (10 mesh to 20 mesh). The actual size of the particles is not critical to the invention, however, smaller particles may be too small and dissolve too quickly. Typically, a majority (greater than 50%) will have a particle size greater than 400 microns.

Additional active ingredients for pool, spa and water treatment may be mixed into the composition. For example, additional active ingredients, such as water clarifiers, scale inhibitors, stabilizers, water softeners, corrosion inhibitors, algaecides, fungicides, binders, or mixtures thereof, may be mixed into the composition. Such ingredients, as well as others, are known to those of skill in the art. Particularly, the additional active ingredient in the present invention includes active ingredient components having known functional properties such as copper sulfate, zinc sulfate, aluminum sulfate, sodium citrate, sodium borate, sodium tripolyphosphate (STPP), sodium hexametaphosphate (SHMP). One particular ingredient is a stabilizer. A suitable stabilizer is magnesium sulfate which is hydrated. A particular magnesium sulfate is magnesium sulfate heptahydrate. In a particular embodiment, the composition will contain 0.1-20% by weight of magnesium sulfate heptahydrate; 0.01-10% by weight of aluminum sulfate; and 0.01-10% by weight of sodium hexametaphosphate. More particularly, a composition may contain 10-20% by weight of magnesium sulfate heptahydrate; 0.1-2.0% by weight of aluminum sulfate; and) 0.1-2.0% by weight of sodium hexametaphosphate, in addition to the calcium hypochlorite and the colored particles.

The compositions of the present invention are also substantially free of surfactants or any other component that could render the recreational water unsuitable for recreational use. For example, the omission of surfactants helps to avoid possible foaming of the water which would render the water unsuitable for recreational use. Reference to "substantially free" means the composition at most contains trace amounts.

As noted above, the compositions of the invention can be in either granular form or in tableted form. In granular form, the composition is a mixture of the calcium hypochlorite particles and the colored particles. In tableted form, the composition may be tableted with different structures. For example, the composition can be tableted so that the colored particles are dispersed homogenously throughout the composition where the calcium hypochlorite is the major or carrier phase. In another embodiment, the composition is tableted with separate distinct layers for the calcium hypochlorite and for the colored particles.

In the granular form, the calcium hypochlorite and the colored particles are manufactured separately and blended together using known techniques. In addition, the additional ingredients could also be added using these blending techniques.

In accordance with the invention, the composition is administered to the body of recreational water in a biocidal effective amount to inhibit microbial growth that can cause unwanted film formation or unwanted clouding of the water. Typically, a biocidal amount is an amount of the composition that provides the body of recreational water with a residual free chlorine level of at least 1 ppm. The free chlorine levels can also be significantly higher on an intermittent basis to provide a shock treatment to the recreational water system. Generally, the residual free chlorine levels for recreational water systems should be less than about 20 ppm and are generally in the range of about 1 to 10 ppm.

As will be apparent to one skilled in the art, the actual method of administering the composition of the invention can be varied. For example, the granules and tablets can be directly added to the recreational water. In the case of granules, an initial flash of color will emanate from the granules that dissipate after a predetermined amount of time once the hypochlorite anions in the water oxidize and bleach the dye to a colorless state. In the case of compacted tablets, an initial flash of color will and continue to emanate from the tablet until the tablet is exhausted or fully dissolved or utilized. As a result of the continued presence of the initial flash of color from the tablet, an end-user noticing the absence of the transient color can then re-add the tableted composition to the water to replenish free chlorine levels, as needed. In another embodiment, the granules or tablets can be added via a dispenser that controls the dissolution rate of the composition thereby providing a sustained initial flash of color to the water. The absence of the transient color will provide a visual signal to the end-user that the composition in the dispenser has been extinguished and needs to be replenished, if necessary.

The following non-limiting examples have been provided to further illustrate the unique advantages of the present invention.

EXAMPLES

Preparation of the Colored Particles.

A solution containing Hiacid Azure Blue 50 percent liquid (Acid blue 9) was provided, which contained about 50% by volume of the Acid blue 9 dye. Sodium Chloride salt particles were provided as well. The solution of the dye was sprayed onto the sodium chloride particles and allowed to dry. Analysis of the particles showed that the salt particles contained about 15% by weight of the dye on the surface of the salt particles.

Preparation of the Calcium Hypochlorite/Colored Particle Blend

The salt particles were then blended with a granular calcium hypochlorite available from HTH containing about 16% magnesium sulfate heptahydrate, forming a composition containing about 5% by weight of the colored particle and 15% by weight of the magnesium sulfate heptahydrate and 80% calcium hypochlorite in a granular form.

Application of the Composition to Recreational Water

A cup (8 oz) of the granular composition was broadcast spread onto the surface of a swimming pool. As the granular composition contacted the water, the water turned from a nearly colorless clear to a bright blue. The bright blue color appeared on the surface of the pool and below the surface of the pool as the granular composition sunk to the bottom of the pool and the dye was released from the composition. The bright blue color lasted approximately 20 seconds and quickly diminished as the calcium hypochlorite oxidized the dye, to a colorless color.

We claim:
1. A method of treating a body of recreational water with a biocidal composition which provides a visual cue to an end-user treating the recreational body of water signifying the effectiveness of the biocidal composition, the method comprises:
  administering to the body of water a biocidal amount of the composition comprising:
  a majority of calcium hypochlorite particles; and
  an effective amount of colored particles comprising, an oxidizable pigment, an oxidizable dye, a composition of an oxidizable pigment and a water soluble material, a composition of oxidizable dye and a water soluble material, or a mixture therof;

wherein the colored particles release the oxidizable pigment and/or the oxidizable dye to the body of the recreational water to provide a transient color emanating from the composition to the recreational water during dissolution of the composition in the body of recreational water, the transient color providing a visual cue signaling biocidal activity of the composition to an end-user; and wherein the composition is substantially free of surfactants to avoid foaming of the water; and allowing the composition to dissolve or disperse in the water to release the pigment or dye into the body of water, providing a transient color to the body of water during dissolution of the composition in the body of water.

2. The method according to claim 1, further comprising detecting an absence of the transient color in the water thereby signaling to the end-user that the composition has been extinguished, and re-administering the composition to the water thereby replenishing the biocidal activity to the recreational water.

3. The method according to claim 1, wherein the water treatment composition is granular, having particles of calcium hypochlorite and the colored particles and the particles are broadcast spread into the body of water.

4. The method according to claim 1, wherein the water treatment composition is granular, having particles of calcium hypochlorite and the colored particles.

5. The method according to claim 1, wherein the composition is a compacted tablet.

6. The method according to claim 1, wherein the colored particles comprise the oxidizable dye and a water soluble material.

7. The method according to claim 6, wherein the oxidizable dye is placed on the surface of the water soluble material.

8. The method according to claim 7, wherein the water soluble material comprises an inorganic salt, a gum or a resin.

9. The method according to claim 8 wherein the water soluble material comprises an inorganic salt.

10. The method according to claim 9, wherein the inorganic salt comprises sodium chloride.

11. The method according to claim 1, wherein the water soluble material comprises a first water soluble material and a second water soluble material, and the oxidizable pigment and/or oxidizable dye is mixed with the second water soluble material to form a mixture, and the mixture is coated onto the first water soluble material.

12. The method according to claim 11, wherein the first and second water soluble material each comprise a salt.

13. The method according to claim 11, wherein the first and second water soluble material are each sodium chloride.

14. The method according to claim 1, wherein the colored particles comprise between about 0.1% by weight to about 10% by weight of the total weight of the composition.

15. The method according to claim 14, wherein the colored particles comprise between about 1% by weight to about 6% by weight of the total weight of the composition.

16. The method according to claim 14, wherein the oxidizable dye comprises between 0.01 and 2.0% by weight of the composition.

17. The method according to claim 1, wherein the calcium hypochlorite particles comprises between 60 and 99.9% by weight of the composition.

18. The method according to claim 17, further comprising up to 30% by weight, based on the total weight of the composition, of additional active components selected from the group consisting of water clarifiers, scale inhibitors, stabilizers, water softeners, corrosion inhibitors, algaecides, fungicides, binders, or a mixture thereof.

19. The method according to claim 17, further comprising:
i) 0.1-20% by weight of magnesium sulfate heptahydrate;
ii) 0.01-10% by weight of aluminum sulfate; and
iii) 0.01-10% by weight of sodium hexametaphosphate.

20. The method according claim 19, wherein the composition comprises between 0.1% and 10% by weight of the colored particles.

21. The method according to claim 20, comprising:
i) 75-85% by weight of the calcium hypochlorite;
ii) 2.0%-6.0% by weight of the colored particles;
iii) 10-20% by weight of magnesium sulfate heptahydrate;
iv) 0.1-2.0% by weight of aluminum sulfate; and
v) 0.1-2.0% by weight of sodium hexametaphosphate.

* * * * *